(12) United States Patent
Bedingfield

(10) Patent No.: US 9,782,577 B2
(45) Date of Patent: Oct. 10, 2017

(54) SOLENOID PINCH VALVE APPARATUS AND METHOD FOR MEDICAL FLUID APPLICATIONS HAVING REDUCED NOISE PRODUCTION

(71) Applicants: Baxter International Inc., Deerfield, IL (US); Baxter Healthcare SA, Glattpark (Opfikon) (CH)

(72) Inventor: John Bedingfield, Largo, FL (US)

(73) Assignees: Baxter International Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 0 days.

(21) Appl. No.: 15/251,405

(22) Filed: Aug. 30, 2016

(65) Prior Publication Data

US 2016/0367794 A1   Dec. 22, 2016

Related U.S. Application Data

(63) Continuation of application No. 12/479,373, filed on Jun. 5, 2009, now Pat. No. 9,435,459.

(51) Int. Cl.
| | |
|---|---|
| *F16K 7/04* | (2006.01) |
| *A61M 39/28* | (2006.01) |
| *F16K 31/04* | (2006.01) |
| *F16K 31/06* | (2006.01) |
| *A61M 1/28* | (2006.01) |

(52) U.S. Cl.
CPC ............ *A61M 39/28* (2013.01); *A61M 1/28* (2013.01); *F16K 7/045* (2013.01); *F16K 31/046* (2013.01); *F16K 31/0672* (2013.01); *F16K 31/0675* (2013.01)

(58) Field of Classification Search
CPC ......... A61M 39/28; A61M 1/28; F16K 7/045; F16K 31/046; F16K 31/0672; F16K 31/0675
USPC ................... 251/7, 129.15, 129.08, 129.05
See application file for complete search history.

(56) References Cited

U.S. PATENT DOCUMENTS

| 3,511,469 A | 5/1970 | Bell |
| 4,173,031 A | 10/1979 | Leichle |
| 4,239,978 A | 12/1980 | Kofink |
| 4,267,430 A | 5/1981 | Downey |

(Continued)

FOREIGN PATENT DOCUMENTS

| DE | 3817770 | 11/1989 |
| DE | 4242432 | 6/1994 |

(Continued)

OTHER PUBLICATIONS

Non-final Office Action dated Aug. 25, 2009 from U.S. Appl. No. 12/036,003.

(Continued)

*Primary Examiner* — Justin Jonaitis
(74) *Attorney, Agent, or Firm* — K&L Gates LLP

(57) ABSTRACT

A low noise solenoid valve system includes a solenoid valve; and a controller configured to perform a power actuation sequence in which power to the solenoid valve undergoes a plurality of cycles that switch from an actuation level power to a hold level power, wherein the actuation level power is increased at each subsequent cycle, and wherein the actuation power level of one of the plurality of cycles is sufficient to fully actuate the solenoid valve.

25 Claims, 6 Drawing Sheets

(56) References Cited

U.S. PATENT DOCUMENTS

| | | | |
|---|---|---|---|
| 4,350,319 A | 9/1982 | Kawata et al. | |
| 4,360,338 A | 11/1982 | Katchka | |
| 4,539,967 A | 9/1985 | Nakajima et al. | |
| 4,616,802 A * | 10/1986 | Tseng | A61M 39/28 251/7 |
| 4,654,538 A | 3/1987 | Lethellier | |
| 4,744,747 A | 5/1988 | Kawamura et al. | |
| 4,780,805 A | 10/1988 | Chewuk et al. | |
| 4,788,415 A | 11/1988 | Whipple, Jr. | |
| 4,823,825 A | 4/1989 | Buechl | |
| 4,843,301 A | 6/1989 | Belanger | |
| 4,908,496 A | 3/1990 | Higgins | |
| 5,008,773 A | 4/1991 | Yoshida et al. | |
| 5,024,417 A | 6/1991 | Voxbrunner | |
| 5,097,402 A | 3/1992 | Kriz et al. | |
| 5,118,077 A | 6/1992 | Miller et al. | |
| 5,153,805 A | 10/1992 | Tennant et al. | |
| 5,194,718 A | 3/1993 | Reiser et al. | |
| 5,270,519 A | 12/1993 | Higgins | |
| 5,442,515 A | 8/1995 | Wallaert | |
| 5,582,278 A | 12/1996 | Wirtz | |
| 5,632,468 A | 5/1997 | Schoenmeyr | |
| 5,637,786 A | 6/1997 | Weber et al. | |
| 5,645,097 A | 7/1997 | Zechmann et al. | |
| 5,647,387 A | 7/1997 | Tsutsui | |
| 5,671,705 A | 9/1997 | Matsumoto et al. | |
| 5,784,245 A | 7/1998 | Moraghan et al. | |
| 5,790,364 A | 8/1998 | Mikami et al. | |
| 5,803,711 A | 9/1998 | Schoenmeyr | |
| 5,815,362 A | 9/1998 | Kahr et al. | |
| 5,815,365 A | 9/1998 | Stege | |
| 5,825,974 A | 10/1998 | Hutton et al. | |
| 5,908,571 A | 6/1999 | Scott | |
| 6,031,210 A | 2/2000 | Wonka | |
| 6,034,358 A | 3/2000 | Higgins | |
| 6,067,490 A | 5/2000 | Ichimaru et al. | |
| 6,233,397 B1 | 5/2001 | Offir | |
| 6,520,382 B2 | 2/2003 | Estelle et al. | |
| 6,522,844 B2 | 2/2003 | Yamane et al. | |
| 6,560,088 B1 * | 5/2003 | Beck | F01L 9/04 251/129.01 |
| 6,614,008 B2 | 9/2003 | Tidrick | |
| 6,674,629 B2 | 1/2004 | Ozawa et al. | |
| 6,725,816 B2 | 4/2004 | Yamaki et al. | |
| 6,772,640 B1 | 8/2004 | Quigley et al. | |
| 6,874,525 B2 | 4/2005 | Kimura et al. | |
| 6,942,469 B2 | 9/2005 | Seale et al. | |
| 7,104,275 B2 * | 9/2006 | Dille | F16K 7/045 137/486 |
| 7,107,976 B2 | 9/2006 | Gu | |
| 7,230,209 B2 | 6/2007 | Sterling | |
| 7,500,962 B2 | 3/2009 | Childers et al. | |
| 7,740,225 B1 | 6/2010 | Estelle | |
| 9,435,459 B2 * | 9/2016 | Bedingfield | F16K 7/045 |
| 2002/0097120 A1 | 7/2002 | Butzmann et al. | |
| 2004/0251440 A1 | 12/2004 | Gnadinger et al. | |
| 2005/0104601 A1 * | 5/2005 | Engelmann | B60T 8/36 324/522 |
| 2005/0105239 A1 | 5/2005 | Satoh et al. | |
| 2007/0213651 A1 | 9/2007 | Busby et al. | |
| 2008/0058712 A1 | 3/2008 | Plahey | |
| 2009/0026397 A1 * | 1/2009 | Evers | F16K 31/06 251/129.04 |
| 2009/0213519 A1 | 8/2009 | Bedingfield | |
| 2009/0213520 A1 | 8/2009 | Bedingfield | |
| 2009/0213521 A1 | 8/2009 | Bedfingfield | |
| 2009/0285696 A1 | 11/2009 | Fries et al. | |

FOREIGN PATENT DOCUMENTS

| | | |
|---|---|---|
| DE | 19606965 | 8/1997 |
| DE | 10150231 | 6/2002 |
| DE | 10329907 | 1/2005 |
| DE | 3543017 | 2/2005 |
| DE | 102006037940 | 2/2008 |
| DE | 102006059624 | 6/2008 |
| DE | 102007023189 | 11/2008 |
| DE | 102006023606 | 11/2011 |
| EP | 0563760 | 10/1993 |
| EP | 0851164 | 1/1998 |
| EP | 1830370 | 9/2007 |
| GB | 2289571 | 11/1995 |

OTHER PUBLICATIONS

Final Office Action dated Dec. 17, 2009 from U.S. Appl. No. 12/036,003.
Non-final Office Action dated Aug. 18, 2009 from U.S. Appl. No. 12/035,998.
Final Office Action dated Jan. 14, 2010 from U.S. Appl. No. 12/035,998.
International Search Report, PCT/US2009/034244.
International Search Report, PCT/US2009/034251.
International Search Report for App. No. PCT/US2010/035730 dated Oct. 21, 2010, pp. 1-8.
Written Opinion for App. No. PCT/US2010/035730 dated Oct. 1, 2010, pp. 1-7.

* cited by examiner

SOLENOID PINCH VALVE APPARATUS AND METHOD FOR MEDICAL FLUID APPLICATIONS HAVING REDUCED NOISE PRODUCTION

CROSS REFERENCE TO RELATED APPLICATIONS

This application is a continuation application that claims priority to and the benefit of U.S. application Ser. No. 12/479,373, filed Jun. 5, 2009, the entire disclosure of which is hereby incorporated by reference herein.

BACKGROUND

The present disclosure relates generally to medical fluid delivery and more particularly to dialysis fluid delivery.

Certain dialysis machines use electrically actuated solenoid valves to open and close fluid flow through associated tubing. Peritoneal dialysis ("PD") is often performed at night while the patient is sleeping. It is accordingly desirable to minimize the acoustical noise that the dialysis machine generates, so as not to disturb the patient while sleeping. Moreover, it is generally desirable to produce equipment that is not noisy.

In many cases, the electrically actuated solenoid valves are of a normally closed type, in which the valves are spring or mechanically actuated closed (to occlude flow) and electrically actuated open (to allow flow). Such configuration provides a "fail safe" valve, which closes the tube, occluding fluid flow upon a loss of power. The spring pushes a plunger of the solenoid valve against the tube to occlude the tube, preventing flow. The spring closing of the valves does not cause significant noise because the valve plunger upon a release of electrical power is pushed against pliable tubing, which cushions the impact of the plunger, preventing significant noise.

Actuation or energizing of the valves, however, results in rapid acceleration of the plunger and a high velocity impact against a magnetic metal body of the solenoid. The impact generates a fairly significant amount of noise, which can wake the patient and be a nuisance generally. While solenoids can be configured to eliminate metal-to-metal contact, the elimination results in a significant increase in the power needed to hold the solenoid in the actuated position. Some solenoids are equipped with a permanent magnet that reduces the hold power to zero. These solenoids however require power to overcome the permanent magnet to close the plunger and tubing and therefore fail to meet the fail safe or power-fail-closed requirement.

A need therefore exists for a solenoid operated pinch valve for medical applications, which reduces actuation noise, without increasing the required hold power, and which operates in a fail safe or fail closed manner.

SUMMARY

The solenoid actuated pinch valve of the present disclosure produces minimal noise when actuated, allowing for overall quiet operation of a medical device, such as a peritoneal dialysis ("PD") machine, which is desirable for PD patients generally and especially those patients who wish to sleep during treatment. In one application, the machine is required to run on battery backup power for a relatively long period of time, such as six hours. It is desirable that the holding power of the solenoid pinch valves is kept to a minimum, so that the battery backup requirement can be met. The metal plunger of the solenoid valve is accordingly allowed to make contact with the metal solenoid body, providing efficient use of the holding power and reducing the overall operational power drain of solenoid pinch valve. The valve also operates a fail safe, spring closed and actuated open manner.

A characteristic of electrically actuated solenoid valves is that the power needed to fully actuate the valve varies based on environmental and other factors, such as temperature, tubing variation, valve unit to unit variation, power supply voltage, and spring wear. It is common practice therefore to apply a power level sufficient to fully actuate the solenoid under a worst case scenario, which is typically more power than is actually needed, causing the high acceleration and high velocity noise producing impact of the valve plunger against the valve body.

The solenoid valve is actuated via a controller. The controller is programmed to initially supply an actuation power that is very likely to be insufficient to fully actuate the plunger even under the best case scenario of environmental and other factors listed above. The initial actuation power moves the plunger some but likely not enough to fully actuate the plunger. Next, the actuation power is reduced to the hold power, which can for example be one-third or less than the actuation power. If the plunger had been fully actuated, the hold power would hold the plunger in the actuated position. But when the plunger is not fully actuated, the hold power will not hold the plunger, and the valve spring forces the plunger back to the closed or occluding position.

The controller applies the hold power momentarily to allow the plunger to be held if fully actuated and then increases the actuation power slightly. Assuming the previous actuation power was insufficient, the increased actuation power moves the solenoid plunger slightly farther in the valve open position than the previous application of actuation power. The power is again reduced to the hold power momentarily to see if the second, slightly increased actuation power is sufficient to fully actuate the plunger.

The above process is repeated until an actuation power is applied that actuates the plunger fully under a worse case scenario of the factors discussed above. In one embodiment, the control algorithm is open loop, that is, the controller does not know which incrementally increased application of actuation power caused the plunger to be fully actuated. What is known is that whichever application of power caused the full actuation was only slightly larger than the previous application of power, which did not cause full actuation. Thus, it can be assumed that the velocity at which the solenoid body fully actuated was very close to zero. The resulting noise produced is accordingly very minimal.

The controller in one embodiment uses pulse-width-modulation ("PWM") to control the incremental increases in power. As described in detail below, the control circuitry in one embodiment includes a microprocessor that provides the PWM signal, which drives the gate of a solenoid driver transistor.

Power is applied at full strength in one embodiment for a certain percentage of the time. The percentage is increased in small increments over a range of percentages that are known to span best case to worst case scenario full actuation percentages. For example, assume it is known that seventy-five percent PWM will not fully actuate the plunger even under a best case scenario of environmental and other factors, and that one hundred percent PWM will fully actuate the plunger even under the worse case scenario of factors. The controller can then be programmed to vary the PWM percentage from fifty to one-hundred percent in one percent increments, totaling twenty-five. The percentage range in one embodiment is great enough to account for variables, such as wear, temperature, and unit to unit variation. It is contemplated to perform the entire sequence in a span of five seconds or less. For example if the solenoid requires 0.2 seconds to cycle through one attempt, and twenty-five attempts are made, twenty-five attempts times 0.2 seconds per attempt equals five seconds for the sequence to complete itself The controller in another embodiment uses PWM but varies pulse magnitude instead of pulse width. Here, the PWM percentage is set, e.g., at fifty percent duty cycle. But instead of setting each pulse at full power, the first pulse is set at a power level that, at fifty percent duty cycle, will not fully actuate the plunger even under a best case scenario of factors. The power level is then increased incrementally to a level that, at fifty percent duty cycle, will fully actuate the plunger at some power level within this range.

It should be appreciated that when the solenoid plunger becomes fully actuated within the guard-banded range, the further increasing of actuation power does not cause noise because the plunger remains fully actuated through the remainder of the control sequence even though the current will at certain times during this remainder period be reduced to the hold current. In one embodiment, the dialysis machine ensures that a tube is loaded before employing the above actuation power control algorithm because without a tube in place the algorithm will cause a loud chattering as the spring repetitiously slams the plunger closed against a wall of the tubeless tube holder.

The repeated partial tube openings allow some flow of fresh or spent fluid prior to full actuation of the solenoid plunger. This small flow of fluid is not problematic for at least two reasons. First, the valve actuation and resulting tube opening takes place once at the initiation of a patient fill or a patient drain sequence only (assuming normal therapy with no alarms, etc.). The small amount of fluid flow due to the actuation power control algorithm is accordingly inconsequential to the overall fill or drain volume. Second, the amount of fluid delivered to or removed from the patient is accounted for gravimetrically in one embodiment, such that the small amount of fluid is weighed and taken into account.

It is accordingly an advantage of the present disclosure to provide a solenoid actuation valve that produces little acoustical noise upon actuation.

It is another advantage of the present disclosure to provide a low noise producing solenoid that has a low holding power requirement.

It is a further advantage of the present disclosure to provide a low noise producing solenoid that fails safe upon power.

DETAILED DESCRIPTION

Figure 1:
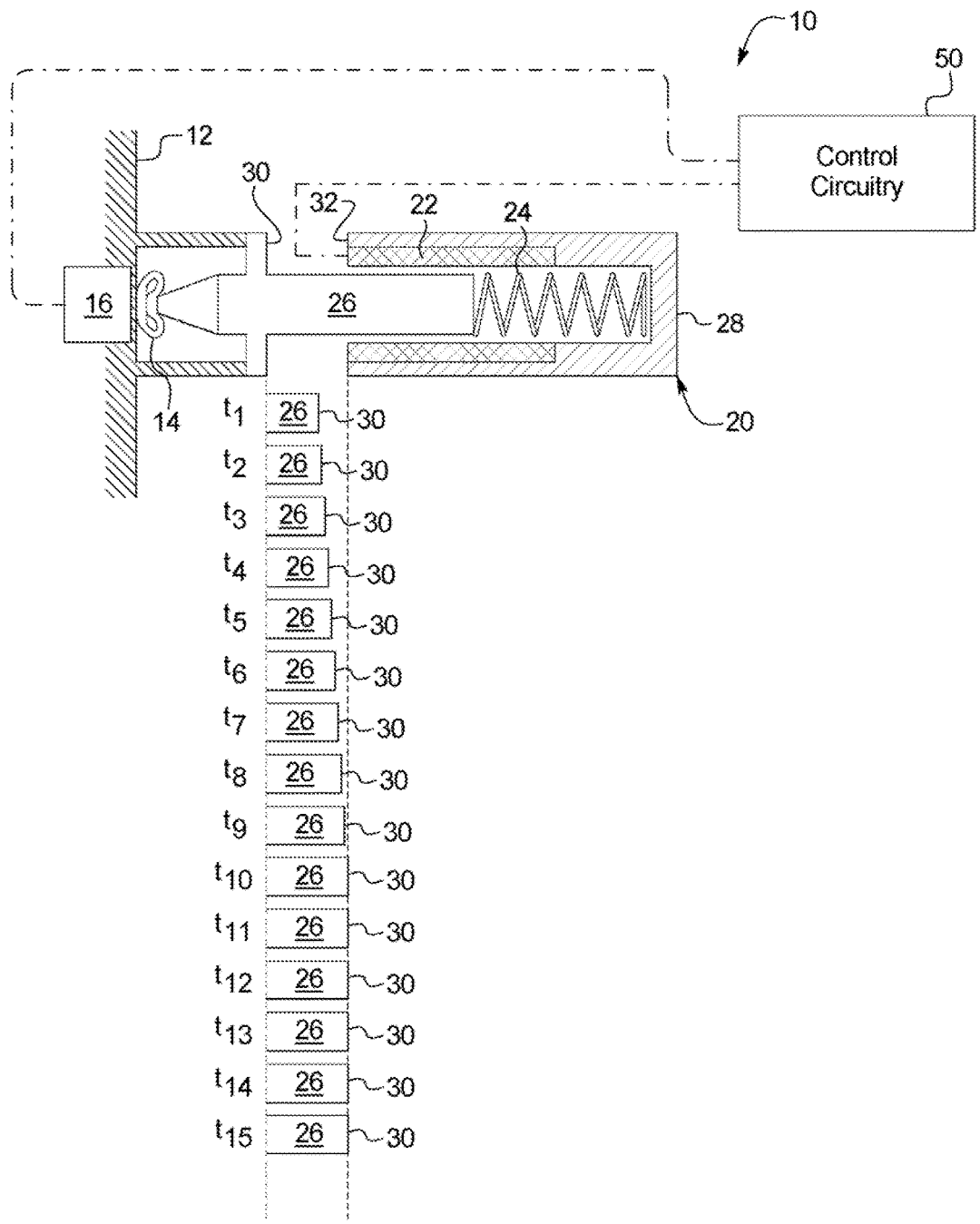
FIG. 1 is a schematic, sectional elevation view illustrating the sequential movement of a solenoid plunger according to the systems and methods of the present disclosure.

Referring now to the drawings and in particular to FIG. 1, one embodiment of the reduced noise solenoid actuation system of the present disclosure is illustrated by system 10. System 10 includes control circuitry 50, which operates one or more solenoid pinch valve 20. Solenoid pinch valve 20 and circuitry 50 in one embodiment are placed inside of a medical fluid delivery machine, such as a peritoneal dialysis, hemodialysis or other type of renal blood therapy machine. It should be appreciated however that system 10 and the various methods disclosed herein for operating system 10 can be used in other medical fluid delivery machines, such as drug infusion pumps or in any application in which it is desirable to reduce noise caused by a solenoid pinch valve. For example, in many peritoneal dialysis ("PD"), the patient undergoes PD treatment at night while sleeping. It is important here to reduce audible noise, so that the machine does not wake or otherwise disturb the patient or partner. With the reduction of noise comes the reduction of wear due to abrupt decelerations caused by the slamming shut of the solenoid plunger against the solenoid housing.

FIG. 1 illustrates a wall or fixture 12 of the application device, such as a dialysis machine wall or fixture. Tube 14 carries fluid, such as dialysate, to and/or from the patient in the case of PD or to or from a dialyzer or blood line in the case of hemodialysis, hemofiltration and hemodiafiltration. Wall 12 is shown generally and can in other embodiments have different shapes, for example, to hold tubing 14 in place. Sensor 16, such as a capacitive or inductive proximity sensor, is fitted to fixture 12 in the illustrated embodiment to sense the presence of tube 14. Sensor 16 sends a signal to control circuitry 50, which can be programmed not to attempt to actuate solenoid valve 20 unless sensor 16 indicates that tube 14 is present.

Solenoid valve 20 in the illustrated embodiment is a spring-closed, actuated-open solenoid pinch valve. That is, when control circuitry 50 does not apply current or power to a coil 22 of solenoid valve 20, spring 24 pushes a plunger 26 of solenoid valve 20 towards wall 12 to close or occlude tubing 14. When control circuitry 50 does apply current or power to coil 22, coil 22 creates a magnetic field around plunger 26 causing plunger 26 to move, in this case to the right, compressing spring 24 and allowing tube 14 to open and dialysate, drug or other medical liquid.

Solenoid valve 20 includes a housing 28, shown here in cross-section for convenience. When valve 20 becomes fully actuated, a plate or end 30 of plunger 26 is pressed up against a portion 32 of housing 28. As discussed above, in known solenoid valves it is common to apply a power level sufficient to fully actuate plunger 26 under a worst case scenario, taking into consideration factors such as temperature, tubing variation, valve unit variation, power supply and spring ware. The applied current or power in many instances is more than is needed to fully actuate plunger 26 under the actual operating conditions. The result is that endplate 30 is slammed against portion 32 of housing 28, causing a relatively significant amount of audible noise. Control circuitry 50 and the methodology discussed here solve this problem.

FIG. 1 is helpful because it illustrates visually the impact of control circuitry 50, and the methodology discussed herein, on plunger 26 as system 10 carries out the methodology. Plunger 26 is shown again figuratively in sequence below solenoid valve 20 to illustrate the end of travel of endplate 30 of plunger 26 at the end of a pulse of current or power provided via control circuitry 50. In particular, at time $t_1$, control circuitry 50 has supplied an initial input of power to coil 22. This initial input of power is in one embodiment set to be lower than an expected amount of power needed to fully actuate plunger 26 under a best case scenario of the factors described herein. That is, the power inputted to coil 22 at time $t_1$ is expected not to fully actuate plunger 26. At the end of time $t_1$, control circuitry 50 then applies a hold current to coil 22. As is known in the art, when plunger 26 becomes fully actuated, the amount of current necessary to maintain plunger 26 in the fully actuated position is significantly less (e.g., 20 percent of) the actuation current. But because plunger 26 is not fully actuated after time $t_1$, when control circuitry 50 applies the hold current, spring 24 pushes plunger 26 back to the occluded position shown in FIG. 1.

Plunger returns 26 to the completely occluded position in a situation in which solenoid valve 20 requires a much higher actuating current than holding current, making the valve highly non-linear in this respect. At the point of complete actuation, end 30 of plunger 26 makes metal-to-metal contact with portion 32 of housing 28, which closes the magnetic circuit and allows for a much reduced holding current due to highly increased magnetic efficiency. Spring 24 is preloaded so that plunger 26 does not begin to move until enough starting current is flowing to overcome the spring. As movement begins, the magnetic efficiency increases, so that plunger 26 continues to move to full actuation once the starting current level is reached.

Next, control circuitry 50 increments the current inputted to coil 22 by a small amount, e.g., ten mA. The following figures and associated disclosure illustrate in detail different methods for increasing the input. In any case, at time $t_2$ plunger 26 is shown in its furthest actuated position for this second application of power, here showing end 30 coming closer to housing portion 32 than did end 30 at time $t_1$. However, the amount of power inputted to coil 22 in this second attempt still does not actuate plunger 26 fully. Accordingly, when the lower hold current is applied again, spring 24 pushes plunger 26 back to the occluded position shown in FIG. 1. Control circuitry 50 repeats this process as shown at times $t_3$ to $t_{10}$, each time end 50 of plunger 26 comes increasingly closer to the fully actuated position, at which point end 30 is butted against housing portion 32.

As illustrated, at the end of the power pulse of time $t_9$, end 30 of plunger 26 comes very close to being fully actuated. Then at time $t_{10}$, which is the end of the next power pulse, plunger 26 becomes fully actuated, such that when the hold current is thereafter applied, plunger 26 remains fully actuated, allowing flow through tubing 14. The slight incremental power increase between times $t_9$ and $t_{10}$ ensures that the power applied just barely enables plunger 26 to become fully actuated, and ensures that end 30 of plunger 26 is at close to a zero velocity when it impacts portion 32 of housing 28. There is accordingly a significant reduction in the amount of audible noise due to the opening of valve 20.

As seen in FIG. 1, the system and method of the present disclosure continues to attempt to actuate the plunger 26 at times $t_{11}$ to $t_{15}$, increasing power each time, until a final attempt is made at $t_{15}$ using a power that is expected to fully actuate plunger 26 under any set of conditions discussed above. This power level could be the power level applied in known solenoid systems, which is in most cases more than needed under the actual conditions. With plunger 26 fully actuated, the hold current in between will maintain the plunger in the fully actuated state, such that plunger 26 does not chatter against wall portion 32. The differences in time between time segments $t_1$ and $t_2$, and so on, is on the order of milliseconds, such that the entire sequence from $t_1$ to $t_{15}$ is a relatively short period of time.

The tubing 14 is made of a soft, compliant material, such that the repeated closing of tubing 14 does not produce audible noise. Also, the medical device employing system 10 in one embodiment employs weigh scales to measure how much fluid is delivered to or removed from a patient or dialyzer, such that the medical machine accounts for the small amount of fluid that flows through tubing 14 as plunger 26 chatters back and forth from time $t_1$ to time $t_{10}$. Further, in systems such as peritoneal dialysis systems, the sequence shown in FIG. 1 is only performed once per patient fill or patient drain, such that the very small amount of fluid as compared to the overall fill or drain volume is insignificant.

Figure 2:
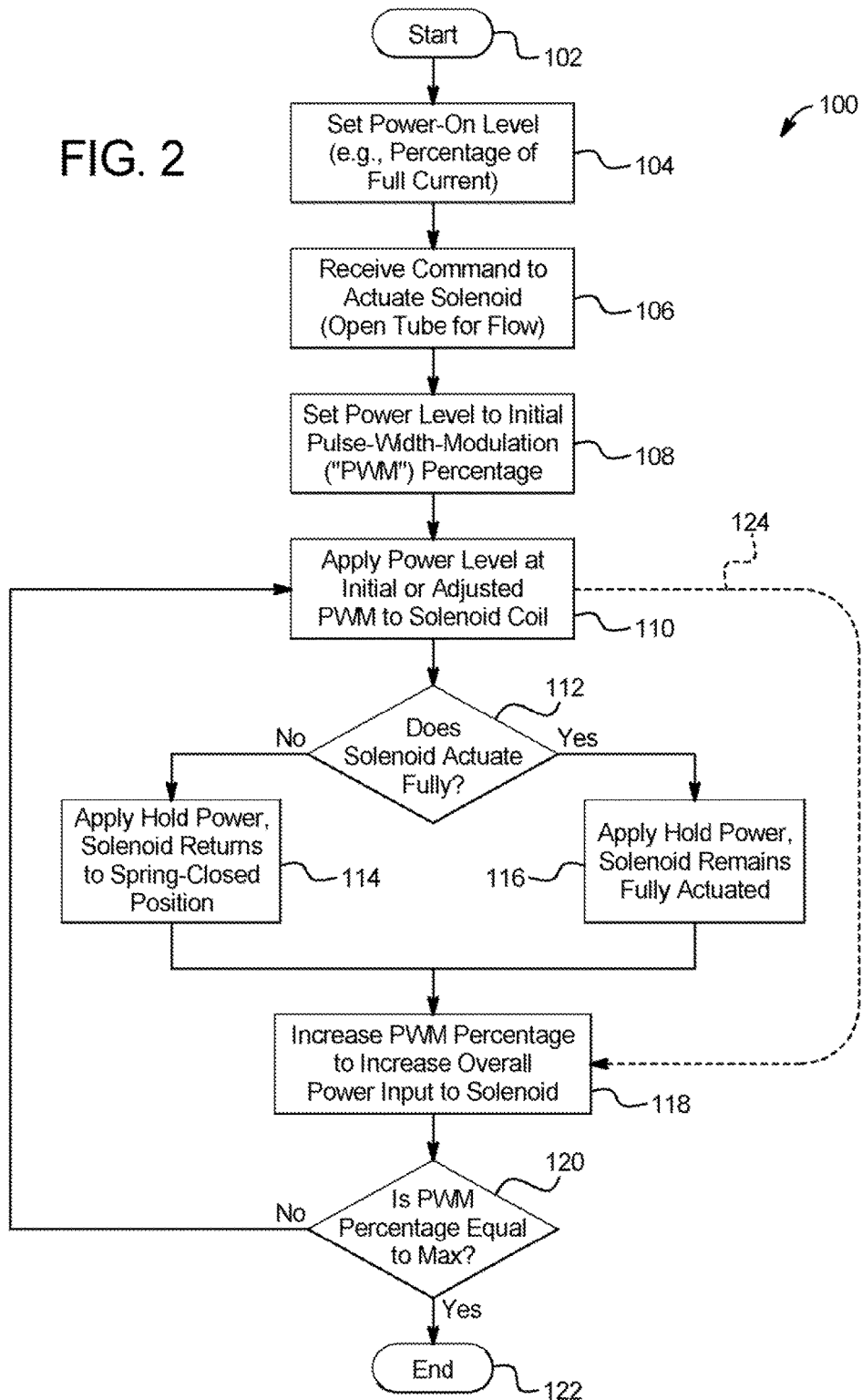
FIG. 2 is a logic flow diagram illustrating one solenoid pinch valve actuation system and method of the present disclosure, which varies pulse-width-modulation ("PWM") percentage.

Referring now to FIG. 2, logic flow diagram 100 illustrates one method or algorithm for incrementally increasing the current or power to solenoid coil 22 to achieve the sequence of solenoid actuations to achieve reduced noise for plunger 26 opening as discussed above in connection with FIG. 1. Methodology 100 starts at oval 102 and sets a power-on level of current at block 104. This can be a percentage of full current. In one embodiment, the power-on level of current for methodology 100 is one hundred.

At block 106, system 10 employing methodology 100 receives a command to actuate solenoid valve 20, for example, to open tube 14 to allow fluid flow. It is expected that the circuitry 50 of system 10 is provided on a subcontroller or printed circuit board, which interacts with one or more supervisory controller. The command to actuate solenoid valve 20 can come from such supervisory controller and be sent to a microprocessor of the subcontroller or circuitry 50 of system 10. The setting of the power-on level at block 104 and the setting of the PWM level discussed next in connection with block 108 can be preset, such that the order of blocks 104 to 108 is unimportant.

Figure 3:
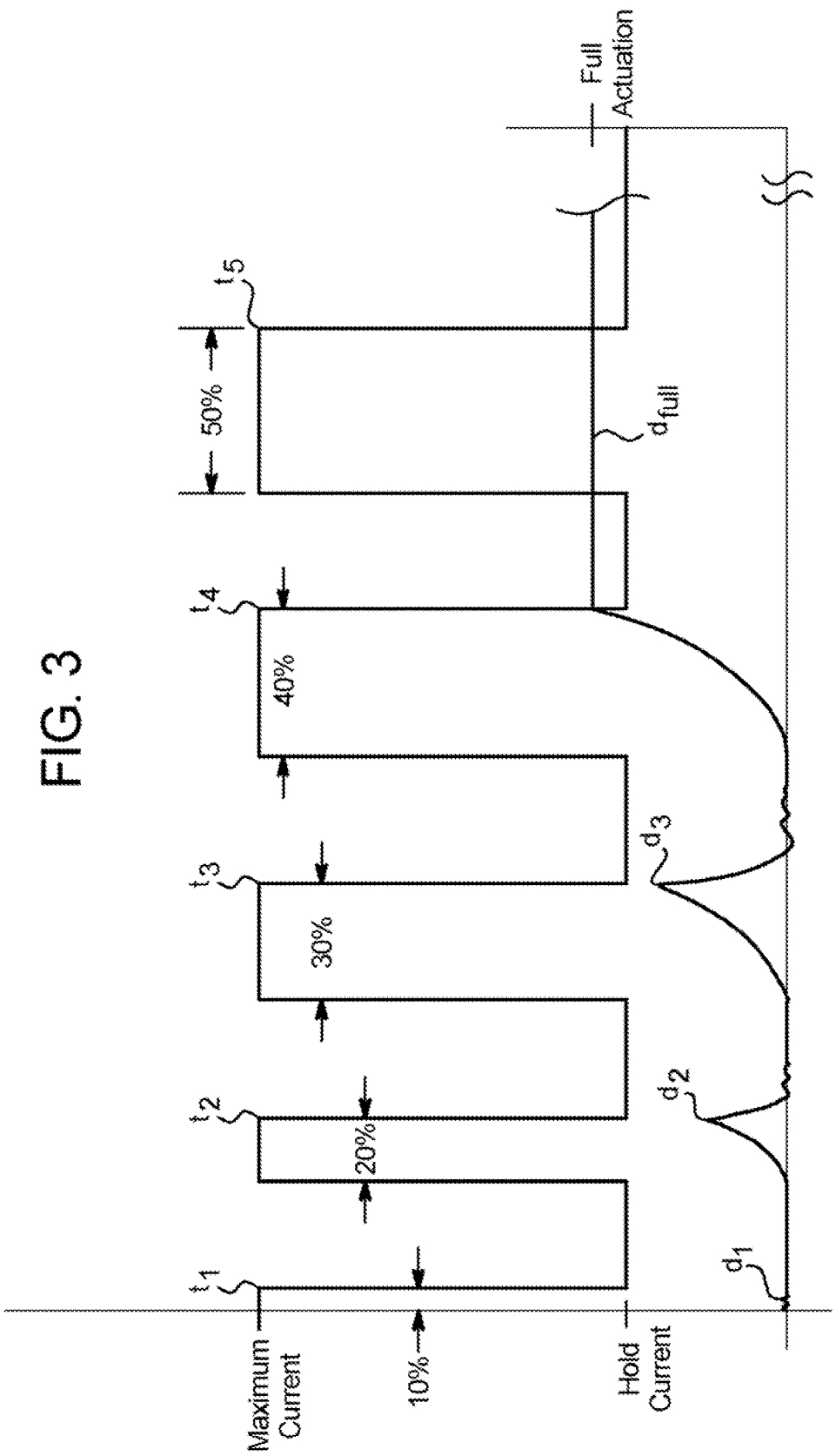
FIG. 3 is a graph depicting varying PWM percentages and corresponding solenoid plunger openings.

At block 108, system 10 employing methodology 100 sets the power level to an initial pulse-width-modulation ("PWM") percentage. Again, the initial PWM percentage is one in which it is expected that plunger 26 is not fully actuated even under a best case scenario of the above-listed conditions. PWM is known in the art and generally involves the varying of time in which a stepped power input is on verses off. FIG. 3 illustrates this variation of time graphically.

At block 110, system 10 employing methodology 100 applies the power-on level of current set at block 104, at the initial PWM percentage set at block 108, to solenoid coil 22. The input power causes plunger 26 to move as shown in FIG. 1. At diamond 112, methodology 100 determines if solenoid plunger 26 has or has not actuated fully under the power input applied at step 110. One important advantage of system 10 is that the system does not actually need to know whether plunger 26 has been fully actuated. That is, it is possible to incorporate a sensor with valve 20, which detects whether the valve has been fully actuated. However, such sensors and additional circuitry at cost. Thus while the present disclosure does contemplate using a sensor, in one preferred embodiment such sensor is not provided. So, the steps shown at boxes 114 and 116 may not actually be steps carried out by system 10, rather, blocks 114 and 116 show two possible outcomes of the application of the input power applied at block 110. Dashed line 124 illustrates that methodology 100 in one preferred embodiment moves from block 110 to block 118, in which case the increases in PWM percentage are made automatically and regardless of whether plunger 26 is actuated fully.

Block 114 illustrates the scenario in which the applied input power at block 110 is not sufficient to fully actuate plunger 26, in which case spring 24 forces plunger 26 to close to occluded position when hold power is applied. Block 116 illustrates the alternative condition in which the power input supplied at block 110 is sufficient to fully actuate plunger 26, such that the plunger remains actuated when hold current is applied.

If a sensor is provided to detect when the plunger 26 is fully actuated, methodology 100 can end when the fully actuated condition at block 116 is reached. Here, the incremental increase in PWM percentage at block 118 is performed only when the non-fully actuated condition occurs at block 114. Methodology 100 in FIG. 2 however illustrates one preferred embodiment, in which the PWM percentage is increased regardless of whether the condition of block 114 or block 116 is met. Referring again to FIG. 1, assuming system 10 has not reached one hundred percent PWM at the time $t_{10}$, using methodology 100, system 10 continues to increase the PWM percentage to a maximum, e.g., one hundred percent. It should be appreciated though that the maximum PWM may not be one hundred percent and can be any desirable PWM percentage. For example, a range of PWM percentages can range from fifty to sixty percent.

Importantly, when plunger 26 has become fully actuated, a continued application of actuation power and increasingly higher PWM percentages produces no physical effect on plunger 26. Plunger 26 merely remains actuated, as it would if only the hold current had been applied. Eventually, methodology 100 runs through the entire sequence as shown in connection with diamond 120, at which point sequence 100 ends, as shown at oval 122. However, as shown in FIG. 2, until PWM percentage reaches its maximum, an increased PWM percentage power input is applied to solenoid coil at block 110 regardless of whether the plunger 26 is not fully actuated as seen in connection with block 114 or is fully actuated as seen connection with block 116.

Referring now to FIG. 3, the outcome of methodology 100 is shown graphically. Here, the distance that the plunger 26 moves d is graphed in relation to time t, which marks the end of a modulated pulse of power. For illustrated purposes, PWM percentage is increased by 10 percent in each cycle of the sequence. It is expected that the increase may be much smaller, such as one or two percent. Further, the total expected range of increases may be, for example, seventy-five to one-hundred percent.

FIG. 3 also illustrates the power-on current to be the maximum allowable power-on current. It should be appreciated however that the power-on current may be at a level less than maximum current. In FIG. 3, however, it should noted that the power-on current is the same for each sequential increased percentage. It is contemplated, if desired, to also vary power-on current in combination with varying PWM percentage.

As seen in FIG. 3, at the end of time $t_1$ at PWM percentage of ten, solenoid plunger 26 moves very little as seen by $d_1$. At time $t_2$ corresponding to twenty percent PWM, a slightly increased d2 is reached as plunger 26 moves in a parabolic manner upwardly towards full actuation and then drops dramatically when power is reduced and resonates in a sinusoidal manner about zero distance moved. It is expected that due to the compliance of tubing 14, the movement of plunger 26 will dampen to a stop as illustrated in FIG. 3. At the time $t_3$ corresponding to a thirty percent PWM, plunger 26 moves parabolically even closer to full actuation and then dampens out quickly when power is reduced to hold level. At time $t_4$, plunger 26 moves to full actuation as seen by $d_{full}$, and remains at $d_{full}$ when power is reduced to hold level after time $t_4$.

FIG. 3 illustrates one preferred implementation of methodology 100, in which system 10 continues to increase PWM as shown by the increase in percentage to fifty percent ending at time $t_5$, and so on. As discussed, such additional increases have no effect on the movement of solenoid plunger 26, which reached $d_{full}$ at time $t_4$, and remained at $d_{full}$ at time $t_5$ and so on. Eventually, methodology 100 reaches maximum PWM, at which time current is steadied at the hold current level until a controller, e.g., supervisory controller in communication with a subcontroller, for system 10 removes the hold current and allows plunger 26 to occlude tubing 14.

Figure 4:
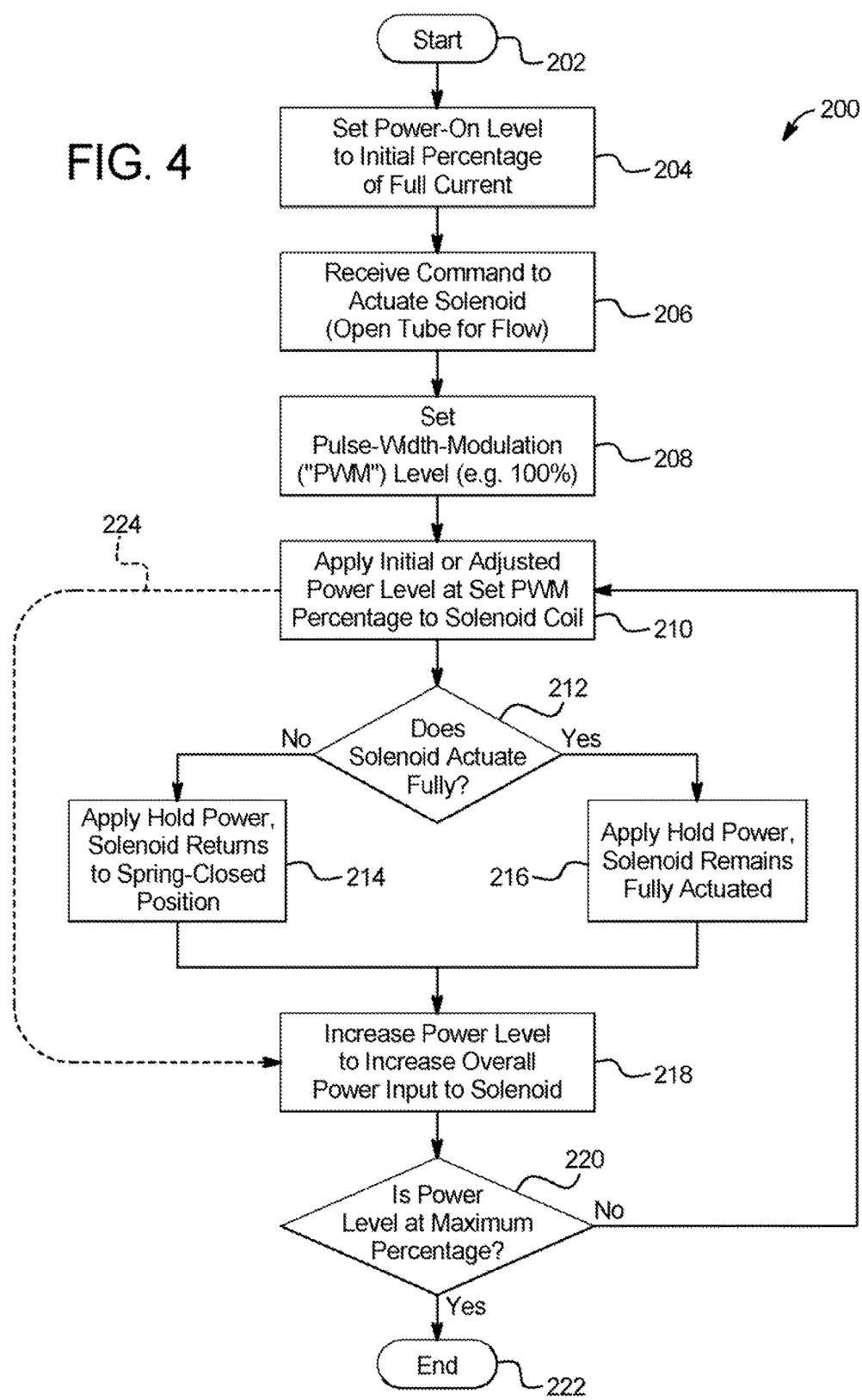
FIG. 4 is a logic flow diagram illustrating another solenoid pinch valve actuation system and method of the present disclosure, which varies percentages of maximum current inputted to the solenoid.

Referring now to FIG. 4, logic flow diagram 200 illustrates another method or algorithm for incrementally increasing the current or power to solenoid coil 22 to achieve the sequence of solenoid actuations to achieve reduced noise for plunger 26 opening as discussed above in connection with FIG. 1. Methodology 200 starts at oval 202 and sets a power-on level of current at block 204. The power-on level of current at block 204 is a percentage of full current, which is less than one hundred percent, e.g., fifty percent or less.

At block 206, system 10 employing methodology 200, e.g., running on a subcontroller, receives a command to actuate solenoid valve 20, e.g., from a supervisory controller, to open tube 14 to allow fluid flow. The setting of the power-on level at block 204 and the setting of the PWM level discussed next in connection with block 208 can be preset, such that the order of blocks 204 to 208 is unimportant.

At block 208, system 10 employing methodology 200 sets the power level to a constant pulse-width-modulation ("PWM") percentage, e.g., fifty percent. Again, the initial power-on level running at the constant PWM percentage is one in which it is expected that plunger 26 is not fully actuated even under a best case scenario of the above-listed conditions.

At block 210, system 10 employing methodology 100 applies the initial power-on level of current set at block 204, at the constant PWM percentage set at block 208, to solenoid coil 22. The input power causes plunger 26 to move as shown in FIG. 1. At diamond 212, methodology 100 determines if solenoid plunger 26 has or has not actuated fully under the power input applied at step 210. Again, an important advantage of system 10 is that the system does not actually need to know whether plunger 26 has been actuated fully, and thus does not require (although it can use) position detection. So again, the steps shown at boxes 214 and 216 may not actually be steps carried out by system 10, rather, blocks 214 and 216 show two possible outcomes of the application of the input power applied at block 210. Dashed line 224 illustrates that methodology 200 in one preferred embodiment moves from block 210 to block 218, in which case the increases in power level percentage are made automatically and regardless of whether plunger 26 is actuated fully.

Block 214 illustrates the scenario in which the applied input power at block 210 is not sufficient to fully actuate plunger 26, in which case spring 24 forces plunger 26 to close to occluded position when hold power is applied. Block 216 illustrates the alternative condition in which the power input supplied at block 210 is sufficient to fully actuate plunger 26, such that the plunger remains actuated when hold current is applied.

If a sensor is provided to detect when the plunger 26 is fully actuated, methodology 200 can end when the fully actuated condition at block 216 is reached and hold power is applied. Here, the incremental increase in power level percentage at block 218 is performed if only when the non-fully actuated condition occurs at block 214. Methodology 200 in FIG. 4 however illustrates one preferred embodiment, in which the power level percentage is increased regardless of whether the condition of block 214 or block 216 is met. Referring again to FIG. 1, assuming system 10 has not reached one hundred percent power level at the time $t_{10}$, using methodology 200, system 10 continues to increase the power level percentage to a maximum, e.g., one hundred percent. It should be appreciated though that the maximum power level may not be one hundred percent and can be any desirable power level percentage. For example, a range of power level percentages can range from 50 to 60 percent.

Importantly, like above with PWM modification of method 100, when plunger 26 has become fully actuated, a continued application of actuation power and increasingly higher power level percentages produces no physical effect on plunger 26. Plunger 26 merely remains actuated, as it would if only the hold current had been applied. Eventually, methodology 200 runs through the entire sequence as shown in connection with diamond 220, at which point sequence 200 ends, as shown at oval 222. However, as shown in FIG. 4, until power level percentage reaches its maximum, an increased power level percentage is applied to solenoid coil at block 210 regardless of whether the plunger 26 is not fully actuated as seen in connection with block 214 or is fully actuated as seen connection with block 216.

Figure 5:
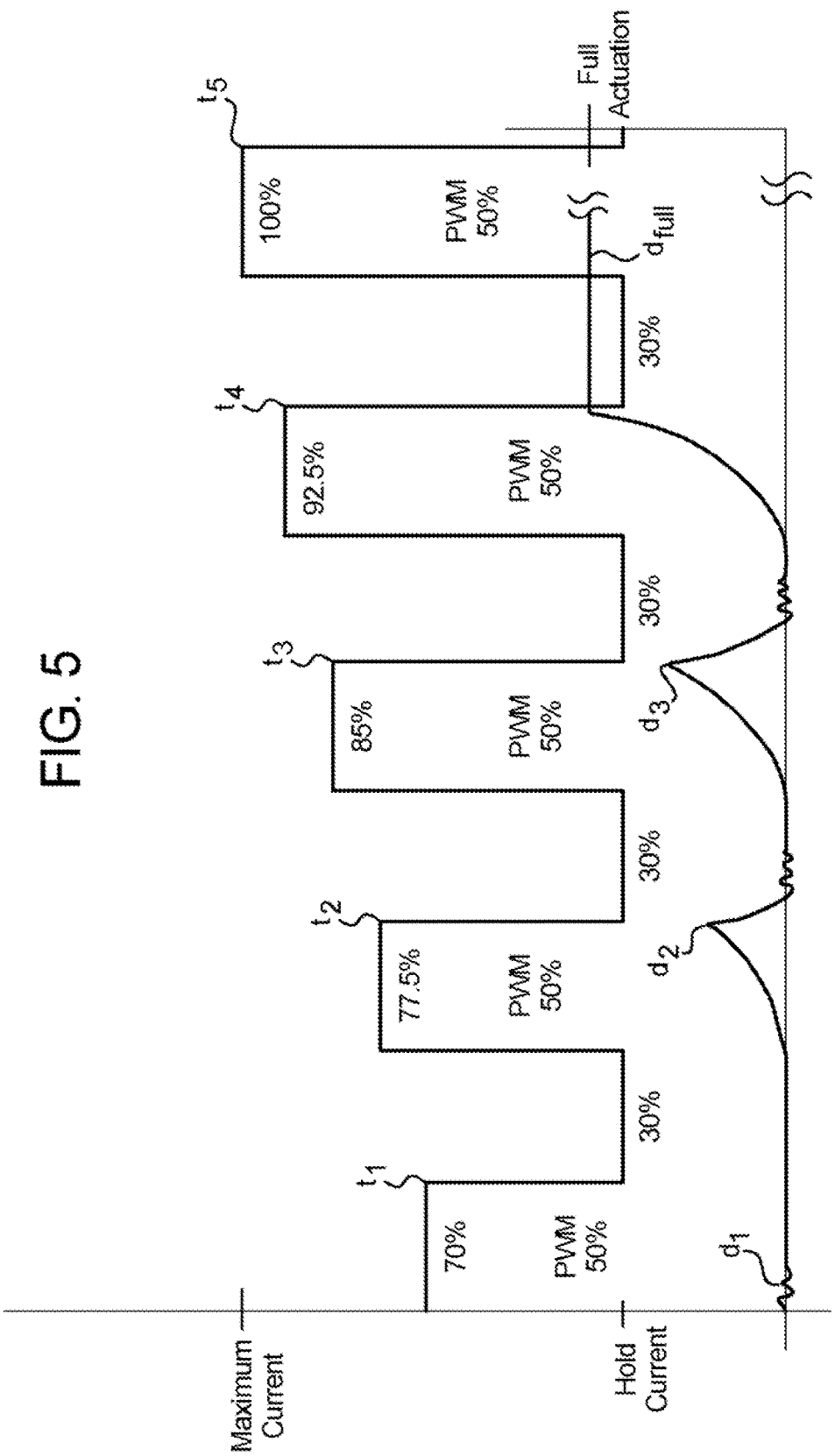
FIG. 5 is a graph depicting varying percentages of maximum current and corresponding solenoid plunger openings.

Referring now to FIG. 5, the outcome of methodology 200 is shown graphically. Here, the distance that the plunger 26 moves d is graphed in relation to time t, which marks the end of a modulated pulse of power. For illustrated purposes, hold current is set to thirty percent power level is set initially at seventy percent and is increased by 7.5 percent in each cycle of the sequence. It is expected that the increase may be much smaller, such as one percent. Further, the total expected range of increases may be, for example, twenty-five percent. Still further alternatively, the increases in power level may be done in units of power or current instead of percentages.

FIG. 5 also illustrates that the PWM percentage is set at a constant fifty percent. It should noted that the PWM is the same for each sequential increased percentage. As discussed above, if desired PWM can be varied, e.g., increased, in combination with varying PWM percentage.

As seen in FIG. 5, at the end of time $t_1$ at power level percentage of seventy, solenoid plunger 26 moves very little as seen by $d_1$. At time $t_2$ corresponding to 77.5 percent power level, increased d2 is reached as plunger 26 moves in a parabolic manner towards full actuation and then drops dramatically and resonates sinusoidally about zero distance moved when power is reduced to hold level. It is expected that due to the compliance of tubing 14, the movement of plunger 26 will dampen to a stop as illustrated in FIG. 5. At the time $t_3$ corresponding to a thirty percent power level, plunger 26 moves in a parabolic manner even closer to full actuation and then dampens out quickly when power is reduced. At time $t_4$, plunger 26 moves in a parabolic manner to full actuation as seen by $d_{full}$, and remains at $d_{full}$ when power is reduced to the hold current after time $t_4$.

FIG. 5 illustrates one preferred implementation of methodology 200, in which system 10 continues to increase power level as shown by the increase in percentage to one hundred percent ending at time $t_5$. As discussed, such additional increases have no effect on the movement of solenoid plunger 26, which reached $d_{full}$ at time $t_4$, and remained at $d_{full}$ at time $t_5$. Methodology 200 reaches maximum power level at $t_5$, after which current is steadied at the hold current level until a controller, e.g., supervisory controller in communication with a subcontroller, for system 10 removes the hold current and allows plunger 26 to occlude tubing 14.

Figure 6:
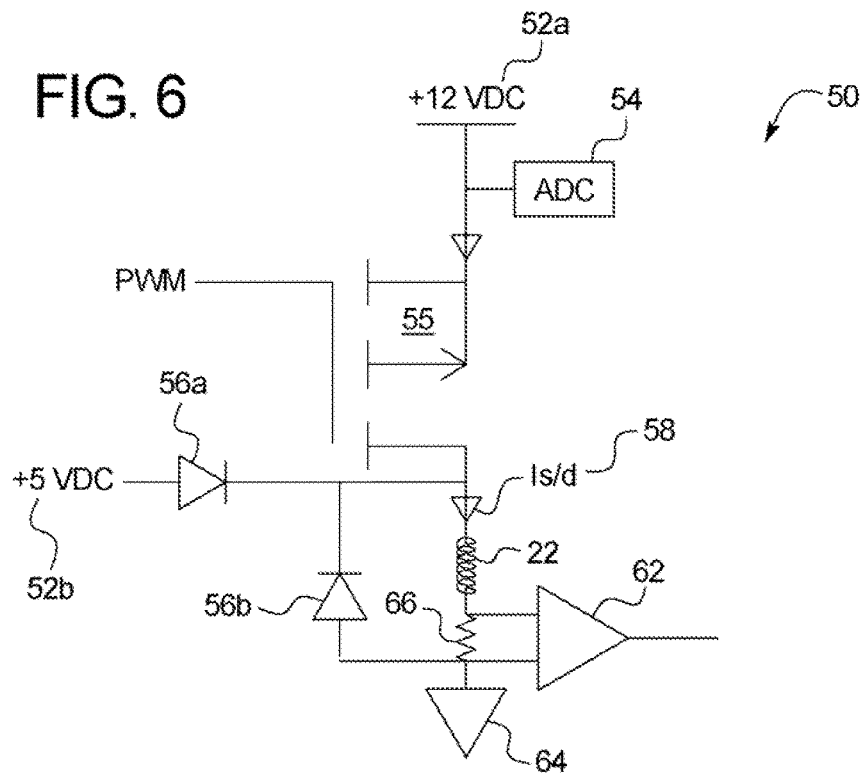
FIG. 6 is a schematic view of one suitable circuitry for the systems and methods of the present disclosure.

Referring now to FIG. 6, circuitry 50 illustrates one suitable circuit for system 10. Circuitry 50 includes a first DC power supply 52a, e.g., twelve VDC, which supplies current to solenoid coil 22, and a second DC power supply 52b, e.g., five VDC, which supplies the hold current to solenoid coil 22. Analog to digital converter ("ADC") 54 digitizes the actual voltage of power supply 52a, so that the voltage can be measured to allow PWM compensation for supply voltage variation. Diode 56a is a blocking diode that prevents current flow from power supply 52a to power supply 52b whenever FET switch 55 is closed. FET switch 55 has a PWM signal driving gate. Diode 56b is provided to allow current to continue to flow through the solenoid coil 22 during the portion of the PWM cycle when the FET switch 55 is open and before the current from supply 52b to solenoid coil 22 drops to a hold level. Line 58 carries the solenoid current. Resister 66 is a current sense resistor to measure current 58 flowing through solenoid coil 22. Amplifier 62 amplifies the voltage across current sense resistor 66 to a level that a second ADC (not shown) can digitize so as to be measured. Ground 64 is the return path for all currents that supplies 52a and 52b pass through coil 22 and current sense resistor 66. When solenoid valve 20 is to be released after actuation, power supply 52b is turned off or disconnected.

Figure 7:
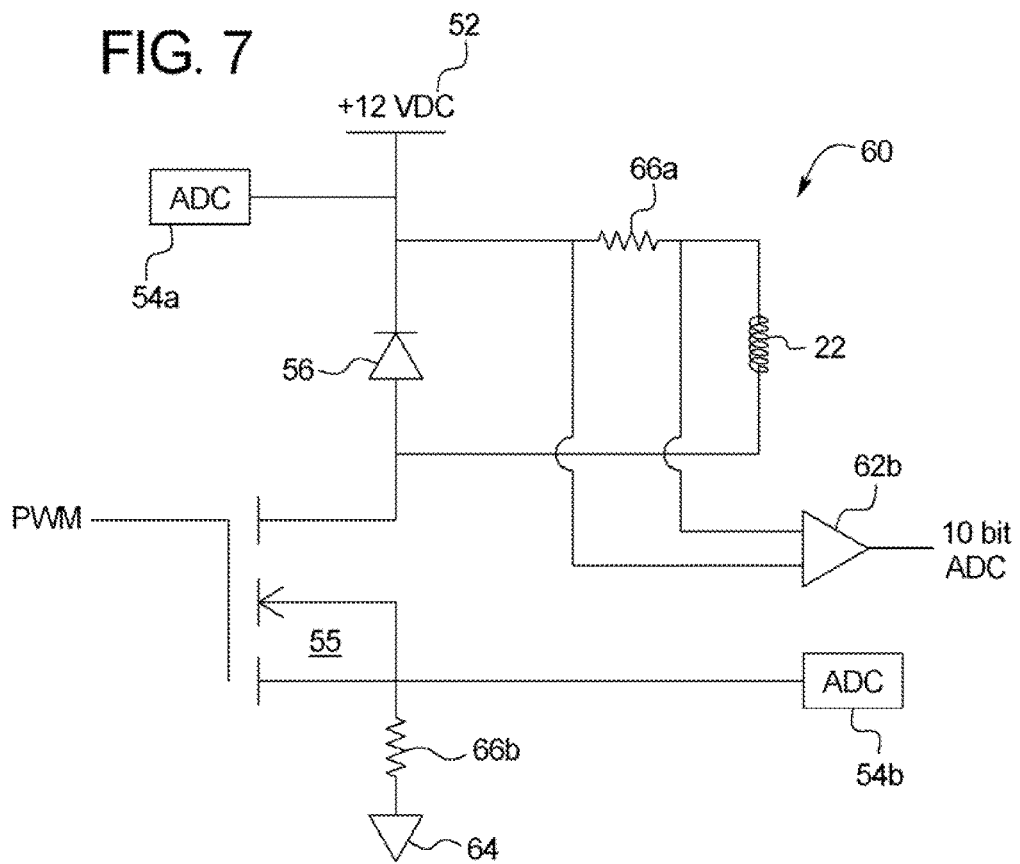
FIG. 7 is a schematic view of another suitable circuitry for the systems and methods of the present disclosure.

Referring now to FIG. 7, circuitry 60 illustrates another suitable circuit for system 10. Here too, FET 55 includes a gate driven by a PWM signal. Circuitry 60 includes a DC power supply 52, e.g., twelve VDC, which supplies current to power solenoid coil 22. ADC 54a operates the same as ADC 54 of circuitry 50 of FIG. 6. Diode 56 allows current to continue to flow through solenoid coil 22 during the portion of the PWM cycle when the FET switch 55 is off. Current sense resistor 66a supplies to amplifier 62 a voltage proportional to current passing through coil 22. Current sense resistor 66b provides an alternative means of measuring solenoid current during the portion of the PWM cycle when the FET switch 55 is closed. ADC 54b reads the voltage across the current sense resistor 66b, has the advantage of not requiring a differential input amplifier, but has the disadvantage of only being able to measure coil 22 current during periods when FET switch 55 is on. ADC 54b has the further advantage of being able to detect a high current associated with a shorted diode 56. Ground 64 is the return path for all currents supplied by power supply 52.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention claimed is:

1. A medical fluid delivery machine comprising:
   a solenoid valve; and
   a controller configured to perform a power actuation sequence in which power to the solenoid valve undergoes a plurality of cycles that switch from an actuation power level to a hold power level, wherein the actuation power level is increased at each subsequent cycle, and wherein the actuation power level of at least one of the plurality of cycles is sufficient to fully actuate the solenoid valve.

2. The medical fluid delivery machine of claim 1, wherein the medical fluid delivery machine is configured to perform at least one of dialysis, hemofiltration, hemodiafiltration, or peritoneal dialysis, and wherein the solenoid valve is operable with a tube carrying blood or a treatment fluid.

3. The medical fluid delivery machine of claim 1, wherein the plurality of cycles includes a predetermined number of cycles.

4. The medical fluid delivery machine of claim 1, wherein the actuation power level of each of the cycles after the cycle that fully actuates the solenoid valve is greater than needed to fully actuate the solenoid valve, the subsequent cycles non-noise producing because the solenoid valve has already been fully actuated.

5. The medical fluid delivery machine of claim 1, wherein the solenoid valve includes a valve plunger, the valve plunger at each of the cycles prior to the cycle that fully actuates the solenoid valve returning to a valve closed position.

6. The medical fluid delivery machine of claim 5, wherein the solenoid valve is positioned adjacent to a tube, the tube cushioning the valve plunger each time the plunger returns to the valve closed position.

7. The medical fluid delivery machine of claim 5, wherein the valve plunger becomes fully actuated at a velocity close to zero.

8. The medical fluid delivery machine of claim 1, wherein the hold power level is the same for each cycle.

9. The medical fluid delivery machine of claim 1, wherein at least one of: (i) the actuation power level of the first cycle of the plurality of cycles is insufficient to fully actuate the solenoid valve under a best case scenario of actuation factors, or (ii) the actuation power level of the last cycle of the plurality of cycles is sufficient to fully actuate the solenoid valve under a worst case scenario of actuation factors.

10. The medical fluid delivery machine of claim 9, wherein the actuation factors include at least one of temperature, tubing vibration, solenoid valve to solenoid valve variation, power supply fluctuation or solenoid valve wear.

11. The medical fluid delivery machine of claim 1, wherein the controller includes a microprocessor in communication with a solenoid driver.

12. The medical fluid delivery machine of claim 1, wherein switching from the actuation power level to the hold power level includes switching from an actuation power pulse width to a hold power pulse width, wherein the actuation power pulse width is increased at each subsequent cycle, and wherein the actuation power pulse width of the at least one of the plurality of cycles is sufficient to fully actuate the solenoid valve.

13. The medical fluid delivery machine of claim 12, wherein an amplitude of at least one of: (i) the actuation power pulse width or (ii) the hold power pulse width is constant.

14. The medical fluid delivery machine of claim 1, wherein switching from the actuation power level to the hold power level includes switching from an actuation power pulse magnitude to a hold power pulse magnitude, wherein the actuation power pulse magnitude is increased at each subsequent cycle, and wherein the actuation power pulse magnitude of the at least one of the plurality of cycles is sufficient to fully actuate the solenoid valve.

15. The medical fluid delivery machine of claim 1, wherein the controller is configured to perform the power actuation sequence by pulsing power to the solenoid valve a plurality of times from a first power level that is selected so as not to fully actuate the solenoid valve, increasing each time towards a second power level that is selected so as to ensure full actuation of the solenoid valve, wherein each pulse of power includes a reduction to a power level below the first power level.

16. The medical fluid delivery machine of claim 1, wherein the solenoid valve includes a plunger opposed by a biasing device, and wherein the controller is configured to perform the power actuation sequence by (i) actuating the plunger against the biasing device a plurality of times at increasing levels of acceleration and (ii) reducing the level of acceleration between the increasing levels of acceleration until one of the levels of acceleration is sufficient to push the plunger against the biasing device to a fully actuated position.

17. The medical fluid delivery machine of claim 16, wherein the controller is configured to increase the level of plunger acceleration from a first level that is selected so as to not fully actuate the plunger to a second level that is selected so as to fully actuate the plunger, the level of acceleration sufficient to push the plunger to the fully actuated position occurring between the first and second acceleration levels.

18. The medical fluid delivery machine of claim 15, wherein the first and second power levels are selected such that full actuation will occur at a power level between the first and second power levels.

19. The medical fluid delivery machine of claim 15, wherein each pulse of power after full activation includes a reduction to a hold power level that maintains the solenoid valve in a fully actuated state.

20. The medical fluid delivery machine of claim 17, wherein the biasing device, at each acceleration level prior to the level of acceleration sufficient to push the plunger to the fully actuated position, pushes the plunger back to an initial position.

21. The medical fluid delivery machine of claim 1, further comprising:
   a sensor positioned and arranged to detect that the solenoid valve is in a fully actuated position, wherein the controller is configured to stop the power actuation sequence and apply the hold power level when the sensor detects that the solenoid valve is in the fully actuated position.

22. A method for medical fluid delivery comprising:
   providing power to a solenoid valve over a plurality of cycles, including
   (i) providing power at an actuation power level,
   (ii) switching from the actuation power level to a hold power level, (iii) repeating (i) and (ii) and increasing, in each subsequent cycle, the actuation power level, and
(iv) fully actuating the solenoid valve when the actuation power level of at least one of the plurality of cycles is sufficient to fully actuate the solenoid valve; and
delivering medical fluid when the solenoid valve is fully actuated.

23. The method of claim 22, which includes determining, after at least one cycle of the plurality of cycles, whether the solenoid valve has fully actuated.

24. The method of claim 22, which includes determining, after at least one cycle of the plurality of cycles, whether the actuation power level is at a maximum level.

25. The method of claim 24, wherein, after the actuation power level reaches the maximum level, the power actuation sequence is completed without determining whether the solenoid valve has fully actuated.

\* \* \* \* \*